US00PP25345P3

(12) United States Plant Patent
Korlipara

(10) Patent No.: US PP25,345 P3
(45) Date of Patent: Mar. 10, 2015

(54) ***COREOPSIS* PLANT NAMED 'BENGAL TIGER'**

(50) Latin Name: ***Coreopsis verticillata* hybrid**
Varietal Denomination: Bengal Tiger

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 180 days.

(21) Appl. No.: 13/815,517

(22) Filed: Mar. 8, 2013

(65) Prior Publication Data

US 2014/0259242 P1 Sep. 11, 2014

(51) Int. Cl.
*A01H 5/00* (2006.01)

(52) U.S. Cl.
USPC ..... Plt./417

(58) Field of Classification Search
USPC ..... Plt./417
See application file for complete search history.

*Primary Examiner* — Anne Grunberg
(74) *Attorney, Agent, or Firm* — Klarquist Sparkman, LLP

(57) ABSTRACT

A new and distinct *Coreopsis* plant named 'Bengal Tiger' characterized by daisy-type inflorescences that grow to 5 cm in diameter, inflorescences that are clear yellow with large dark red eyes, hardy to Zone 6, maybe lower, grass green foliage on short stems, flowering for the whole summer, a low, mounding habit, and excellent vigor.

1 Drawing Sheet

Latin name: *Coreopsis verticillata* hybrid.
Varietal denomination: 'Bengal Tiger'.

BACKGROUND OF THE INVENTION

The present invention relates to a new and distinct *Coreopsis* and given the cultivar name 'Bengal Tiger'. *Coreopsis* is in the family Asteraceae. This new cultivar originated from a controlled breeding program to produce hardy compact *Coreopsis*. The new cultivar originated from planned cross of two proprietary unnamed *Coreopsis verticillata* hybrid seedlings. The new cultivar of *Coreopsis* is a herbaceous perennial to be grown for landscape and container use in a sunny site.

Compared to the parent seedlings the new variety is much shorter with larger flowers and a more upright habit.

Compared to *Coreopsis* 'Route 66', U.S. Plant Pat. No. 20,609, the new cultivar is much shorter with flowers that are yellow with clear dark red eyes rather than creamy yellow with a rose red that bleeds into the creamy yellow. Both are *Coreopsis verticillata* hybrids.

SUMMARY OF THE INVENTION

The following traits have been repeatedly observed and are determined to be the unique characteristics of the new variety. These characteristics in combination distinguish *Coreopsis* 'Bengal Tiger' as a new and distinct cultivar:

1. daisy-type inflorescences that grow to 5 cm in diameter,
2. inflorescences that are clear yellow with large dark red eyes,
3. hardy to Zone 6, maybe lower,
4. grass green foliage on short stems,
5. flowering for the whole summer,
6. a low, mounding habit, and
7. excellent vigor.

This new cultivar has been reproduced only by asexual propagation (cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a nine-month-old *Coreopsis* 'Bengal Tiger' growing in the ground in the trial field in July in Canby, Oreg.

DETAILED PLANT DESCRIPTION

The following is a detailed description of the new *Coreopsis* cultivar based on observations of nine-month-old specimens growing in the trial beds in full sun in Canby, Oreg. Canby is Zone 8 on the USDA Hardiness map. Temperatures range from a high of 95° F. in August to 32° F. in January. Normal rainfall in Canby is 42.8 inches per year. The color descriptions are all based on The *Royal Horticultural Society Colour Chart*, 5$^{th}$ edition.

Plant:

*Type*.—Herbaceous perennial.
*Hardiness*.—USDA Zones 6 to 9.
*Size*.—60 cm wide and 50 cm tall to top of inflorescences.
*Form*.—Mound.
*Vigor*.—Excellent.
*Roots*.—Fibrous, stems root easily from stem cuttings.

Stem:

*Type*.—Ascending, well branched.

*Size*.—Grows to 30 cm tall to where branches for flowering and 8 mm wide.

*Number of stems from the crown*.—6.

*Branching habit*.—Freely branched, an average of 8 lateral branches with secondary branches, branches are opposite in arrangement, new lateral flowering branches are continuously produced throughout the summer.

*Internode length*.—1 cm to 4.5 cm.

*Surface*.—Minutely glandular.

*Color*.—Brown 200A at bottom 7 cm blending to Yellow Green 147B.

Leaf:

*Type*.—Simple.

*Shape*.—Pinnately 3 parted with thread-like segments, to linear on top leaves.

*Arrangement*.—Opposite.

*Size*.—Thread-like segments can spread to 8 cm wide and 6 cm long, the terminal linear segment can grow to 58 mm long and 3.5 mm wide, laterals can grow to 45 mm long and 2 mm wide.

*Apex*.—Acute.

*Margins*.—Entire.

*Petiole*.—0 to 5 mm long and 1 mm wide, Green N137A.

*Surface texture*.—Sparsely pubescent on top and glabrous on bottom side.

*Venation*.—Pinnate, visible main vein the same color as the leaf on both sides.

*Color*.—Topside Green N137A, bottom side Green N137B.

Inflorescence:

*Type*.—Long stalked terminal heads of daisy type inflorescences.

*Peduncle*.—Grows to 7.5 cm long, 1 mm wide, glabrous, Green 137A.

*Size*.—Grows to 4.8 cm wide and 10 mm deep.

*Immature*.—Globular, 6 mm wide and 5 mm deep, Yellow Green148A, glabrous.

*Receptacle*.—Disc shaped, 3 mm wide and 1.5 mm deep, Green 148B.

*Phyllaries*.—In 2 series; first series closet to ray florets in an area 5 mm deep and spreading 8 wide mm wide, 8 in number, each 7 mm long and 2.5 mm wide, lanceolate, margin entire, tip acute, glabrous on both sides, both sides Yellow Green 152A on top ⅓ and 148A on bottom ⅔; lower series in an area 3 mm deep and 12 mm wide, 5 linear lobes, each 6 mm long and 1 mm wide, margin entire, tip acute, top side glandular, bottom side glabrous, both sides Green 137A.

*Self-cleaning*.—Yes.

*Lastingness*.—Each inflorescence lasts about a week on the plant.

Florets:

*Type*.—Composite.

*Ray florets*.—8 in number with no pistil or stamen, grows to 28 mm long, 10.5 mm wide, obovate, with the tip obtuse to shallowly 2 notched, margins entire, glabrous on both sides; topside Yellow 4A on top half blending to Greyed Purple 187B on bottom half with the 187B following up the main veins into the 4A, bottom side Yellow 4A on top half to Greyed Yellow 161A on bottom half.

*Disc*.—Flat becoming rounded with maturity, 8.5 mm wide and becoming 5 mm deep with maturity, Greyed Purple 187B.

*Disc florets*.—Tubular, with stamen and pistil, about 50 in number, 8 mm long and 1 mm wide, tubular; corolla 5.5 mm long, 5 lobed, tube Yellow 4C, lobes Greyed Purple 187A; pistil 1, 8 mm long, ovary 3 mm long, Green Yellow 1C, style 4 mm long, with extruding, 2-branched stigma, stigma and style Yellow Orange 23A; stamen 5, anthers 1.2 mm long, Greyed Brown N199B, pollen Yellow Orange 21A.

*Bloom period*.—June through frost in Canby, Oreg.

*Fragrance*.—Light, *Chrysanthemum*-like.

*Seed*.—None seen.

*Fertility*.—Unknown.

Disease and pests: No pests or diseases have been observed on plants grown under commercial conditions in Canby, Oreg. No resistances are known.

I claim:

1. A new and distinct *Coreopsis* plant as herein illustrated and described.

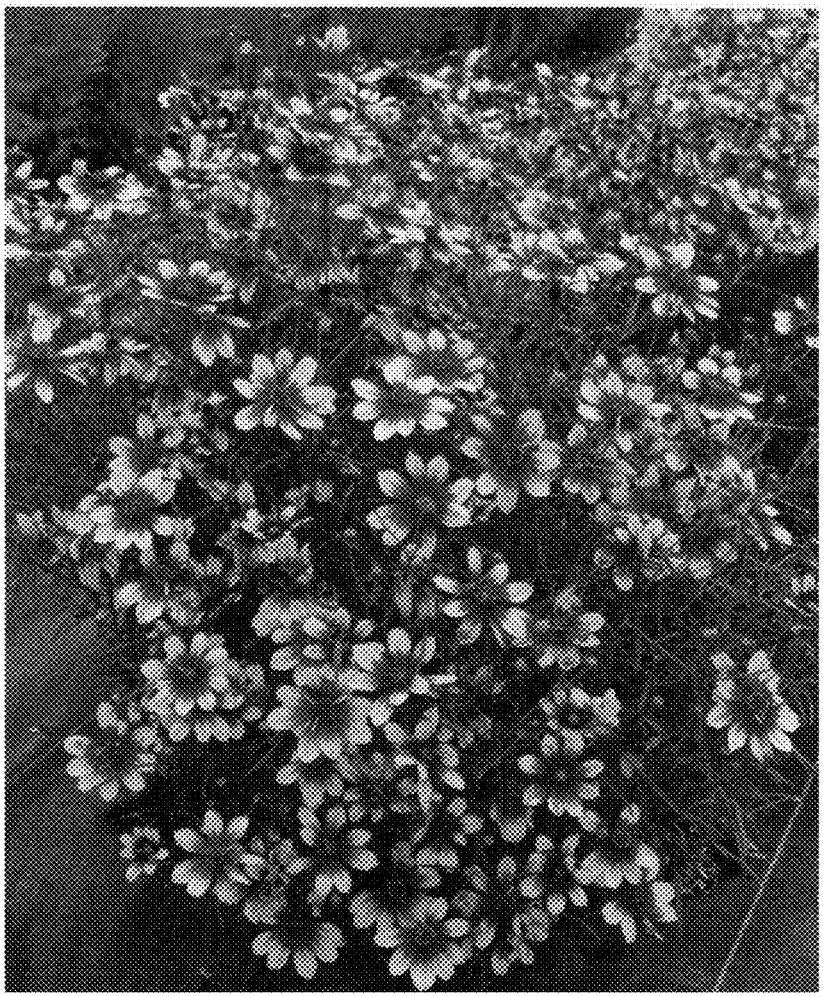

* * * * *